US005700469A

United States Patent [19]
McMichael et al.

[11] Patent Number: 5,700,469
[45] Date of Patent: Dec. 23, 1997

[54] HIV-1 CORE PROTEIN FRAGMENTS

[75] Inventors: Andre James McMichael, Horton-cum-Studley; Douglas Fraser Nixon, Merton College; Alain Robert Michael Townsend, Oxford; Frances Margaret Gotch, Wolvercote, all of England

[73] Assignee: Medical Research Council, London, England

[21] Appl. No.: 474,008

[22] Filed: Jun. 7, 1995

Related U.S. Application Data

[62] Division of Ser. No. 854,629, Jul. 6, 1992, Pat. No. 5,480,967.

[30] Foreign Application Priority Data

Jan. 5, 1990 [GB] United Kingdom ............... 9000287
Feb. 16, 1990 [GB] United Kingdom ............... 9003577

[51] Int. Cl.$^6$ .................. A61K 39/21; A61K 39/12; G01N 33/53; C07K 5/00
[52] U.S. Cl. .................. 424/208.1; 424/204.1; 424/184.1; 424/188.1; 435/5; 435/7.1; 435/7.2; 530/324; 530/325; 530/326
[58] Field of Search .................. 435/5, 7.2, 7.1; 530/324, 325, 326; 424/208.1

[56] References Cited

U.S. PATENT DOCUMENTS

| | | | |
|---|---|---|---|
| 4,554,088 | 11/1985 | Whitehead et al. | 252/62.54 |
| 4,629,783 | 12/1986 | Cosand | 530/324 |
| 4,772,547 | 9/1988 | Heimer et al. | 435/5 |
| 4,808,536 | 2/1989 | Chang et al. | 435/5 |
| 5,395,751 | 3/1995 | McMichael et al. | 435/5 |
| 5,459,238 | 10/1995 | McMichael et al. | 530/326 |
| 5,480,967 | 1/1996 | McMichael et al. | 530/326 |

FOREIGN PATENT DOCUMENTS

| | | |
|---|---|---|
| 230222 | 7/1987 | European Pat. Off. |
| 284587 | 9/1988 | European Pat. Off. |
| 290893 | 11/1988 | European Pat. Off. |
| 330359 | 8/1989 | European Pat. Off. |
| 346022 | 12/1989 | European Pat. Off. |
| 356007 | 2/1990 | European Pat. Off. |
| 412766 | 2/1991 | European Pat. Off. |
| 86/02383 | 4/1986 | WIPO |
| 86/05591 | 9/1986 | WIPO |
| 86/06414 | 11/1986 | WIPO |
| 88/08538 | 3/1988 | WIPO |
| 89/02277 | 3/1989 | WIPO |
| 91/09869 | 7/1991 | WIPO |

OTHER PUBLICATIONS

Butini, et al, 1994, "Comparative Analysis of HIV–Specific CTL Activity in Lymphoid Tissue and Peripheral Blood". Abstract J 306, J. Cell. Biochem. Suppl. 18B.
Webster's Ninth New Collegiate Dictionary, p. 602, 1990.
Sternberg, *FEBS Letters*, vol. 218, pp. 231–237 (1987).
Mills, *J. Immunol.*, vol. 144, pp. 1677–1683 (1990).
Bouillet et al, *Nature*, vol. 339, pp. 473–475 (1989).
Harlow et al, *Antibodies, A Laboratory manual*, Cold Spring Harbor, pp. 77, 96, 97 (1988).
Fauci et al, *Annals of Internal Med.*, vol. 110, pp. 373–385 (1989).
Kurth, *AIDS Research & Human Retroviruses*, vol. 7, pp. 425–433 (1991).
Koup et al, *J. of Virology*, vol. 68, pp. 4650–4655 (1994).
Gotch et al, *International Immunology*, vol. 2, pp. 707–712 (1990).
Choppin et al, *Critical Reviews in Immunology*, vol. 12, pp. 1–16 (1992).
Sanchez–Madrid, *Proc. Natl. Acad. Sci. US*, vol. 79, pp. 7489–7493 (1982).
Ferns et al, *AIDS*, vol. 3, pp. 829–834 (1989).
Mathiesen, *Immunology*, vol. 67, pp. 453–459 (1989).
Wahren et al, *J. Acquired Immune Deficiency Syndrome*, vol. 4, pp. 448–456 (1989).
Parekh et al, *Int. Conf. On AIDs*, Jun. 4–9, 1989, p. 651.
McMichael et al, *J. Exp. Med.*, vol. 164, pp. 1397–1406 (1986).
Gotch et al, *Nature*, vol. 326, pp. 881–882 (1987).
*Cellular and Molecular Immunology*, A.K. Abbas et al Eds., W.B. Saunders Co., Philadelphia, PA, pp. 398–401 (1991).
*Immunology*, Third Ed., I.M. Roitt et al Eds., Mosby, St. Louis, pp. 2.4–2.8 (1993).
Graham et al, *New England J. of Med.*, vol. 333, pp. 1331–1339 (1995).
Haynes, *Science*, vol. 260, pp. 1279–1286 (1993).
Monaco, *Immunology Today*, vol. 13, pp. 173–179 (1992).
Del Val et al, *Cell*, vol. 66, pp. 1145–1153 (1991).
Eisenlohr et al, *J. Exp. Med.*, vol. 175, pp. 481–487 (1992).
Partidos et al, *Immunology*, vol. 77, pp. 262–266 (1992).
Hansen et al, *Fundamental Immunology*, Paul Ed., p. 609 (1993).
Koenig et al, *Nature Med.*, vol. 1, pp. 330–336 (1995).
Meier et al, *Science*, vol. 270, pp. 1360–1362 (1995).
Kerkau er al, *AIDS Res. Human Retro*, vol. 5, pp. 613–620 (1989).
*Immunology at a Glance*, Second Edition, J.H.L. Playfair, Blackwell Scientific Publications, pp. 9–11 (1982).
*Nature Biotechnology*, vol. 14, p. 1527 (1996), "Recombinant Vaccines Inch Closer to the Clinic".
Nixon et al, *AIDS*, vol. 5, pp. 1049–1059 (1991).
Riviere et al, *Journal of Virology*, vol. 63, pp. 2270–2277 (1989).
Townsend et al, *Cell*, vol. 44, pp. 959–968 (1986).
Takahashi et al, *Proc. Natl. Acad. Sci. USA*, vol. 85, pp. 3105–3109 (1988).
Müllbacher et al, *J. Immunological Methods*, vol. 68, pp. 205–215 (1984).

(List continued on next page.)

*Primary Examiner*—Lynette F. Smith
*Attorney, Agent, or Firm*—Oblon, Spivak, McClelland, Maier & Neustadt, P.C.

[57] ABSTRACT

The present invention provides peptidal fragments of human immunodeficiency virus (HIV) which interact specifically with a particular human leucocyte antigen (HLA) class I molecule to stimulate cytotoxic T lymphocyte immunity.

21 Claims, No Drawings

OTHER PUBLICATIONS

Parish et al, *J. Immunological Methods*, vol. 58, pp. 225–237 (1983).

Letter of Opposition to European patent No. 0346022, dated Nov. 13, 1996, from Peter J. Smart to European Patent Office.

Letter of Opposition to European patent No. 0346022, dated Nov. 14, 1996, from Peter J. Smart to European Patent Office.

Communication of Notice of Opposition to European Patent No. 0346022 dated Dec. 23, 1996.

Letter of Opposition to European Patent No. 0412766 dated Dec. 22, 1994, from John Raynor to European Patent Office.

Communication of Notice of Opposition to European Patent No. 0412766 dated Jan. 17, 1995.

Observations of patent proprietor relating to Notice of Opposition to European patent No. 0412766 dated Jun. 23, 1995.

Communication from European Patent Office in Opposition to European Patent No. 0412766 dated Feb. 29, 1996.

Letter from Peter J. Smart to European patent Office iin Opposition to European Patent No. 0412766 dated Sep. 4, 1996.

Walker et al, *Nature*, vol. 328, pp. 345–348 (1987).

*Webster's Ninth New Collegiate Dictionary*, Merriam-Webster, Springfield, MA, pp. 871, 946, 1301 (1988).

Nixon et al, Abstract, *British Society for Immunology Joint Meeting*, "Cytotoxic T Cell (CTL) Response to HIV", Spring 1988.

Wahren et al, *Journal of Virology*, vol. 61, pp. 2017–2023 (1987).

Greene, *Scientific American*, pp. 99–105 (1993).

Brown, *The Washington Post*, Jun. 10, 1993, "AIDS Vaccine Trials Viewed with Caution".

Claverie et al, *Eur. J. Immunol.*, vol. 18, pp. 1547–1553, (1988).

Nixon et al, *Nature*, vol. 336, pp. 484–487 (1988).

Fox, *Bio/Technology*, vol. 12, p. 128 (1994).

Rowland–Jones et al, *Nature Medicine*, vol. 1, pp. 59–63 (1995).

Walker et al, *AIDS*, vol. 4, pp. 177–184 (1990), "Editorial review cytotoxic T lymphocytes against HIV".

Van Kuyk et al, *Journal of Immunology*, vol. 153, pp. 4826–4833 (1994).

Kalams et al, *XI International Conference on AIDS*, "HIV–1–Specific cytotoxic T lymphocyte and Proliferative Responses in Peripheral Blood Mononuclear Cells (PBMC) of Subjects with Stable Non–progressing HIV–1 Infection" Abstracts vol. 1, Mo.A.391, pp. 11–12 (1996).

Buchbinder et al, *XI International Conference on AIDS*, "Long–term Non–progression in the San Francisco City Clinic Cohort", Abstracts vol. 1, Tu.C.553, p. 251 (1996).

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Human immunodeficiency virus ( x i ) SEQUENCE DESCRIPTION: SEQ ID NO:1:

```
Lys Arg Trp Ile Ile Leu Gly Leu Asn Lys Ile Val Arg Met Tyr Cys
1               5                   10                  15
```

( 2 ) INFORMATION FOR SEQ ID NO:2:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Human immunodeficiency virus ( x i ) SEQUENCE DESCRIPTION: SEQ ID NO:2:

```
Val Gln Asn Ala Asn Pro Asp Cys Lys Thr Ile Leu Lys Ala Leu Tyr
1               5                   10                  15
```

( 2 ) INFORMATION FOR SEQ ID NO:3:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Human immunodeficiency virus ( x i ) SEQUENCE DESCRIPTION: SEQ ID NO:3:

```
Cys Gly Ser Glu Glu Leu Arg Ser Leu Tyr Asn Thr Val Ala Thr Leu
1               5                   10                  15
```

( 2 ) INFORMATION FOR SEQ ID NO:4:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Human immunodeficiency virus ( x i ) SEQUENCE DESCRIPTION: SEQ ID NO:4:

Cys Leu Arg Pro Gly Gly Lys Lys Lys Tyr Lys Leu Lys His Ile Val
1               5                   10                  15

( 2 ) INFORMATION FOR SEQ ID NO:5:

( i ) SEQUENCE CHARACTERISTICS:
      ( A ) LENGTH: 16 amino acids
      ( B ) TYPE: amino acid
      ( D ) TOPOLOGY: linear ( i i ) MOLECULE TYPE: peptide ( v i ) ORIGINAL SOURCE:
      ( A ) ORGANISM: Human immunodeficiency virus ( x i ) SEQUENCE DESCRIPTION: SEQ ID NO:5:

Phe Arg Asp Tyr Val Asp Arg Phe Tyr Lys Thr Leu Arg Ala Glu Cys
1               5                   10                  15

( 2 ) INFORMATION FOR SEQ ID NO:6:

( i ) SEQUENCE CHARACTERISTICS:
      ( A ) LENGTH: 16 amino acids
      ( B ) TYPE: amino acid
      ( D ) TOPOLOGY: linear ( i i ) MOLECULE TYPE: peptide ( v i ) ORIGINAL SOURCE:
      ( A ) ORGANISM: Human immunodeficiency virus ( x i ) SEQUENCE DESCRIPTION: SEQ ID NO:6:

Leu Glu Glu Met Met Thr Ala Cys Gln Gly Val Gly Gly Pro Gly Tyr
1               5                   10                  15

( 2 ) INFORMATION FOR SEQ ID NO:7:

( i ) SEQUENCE CHARACTERISTICS:
      ( A ) LENGTH: 12 amino acids
      ( B ) TYPE: amino acid
      ( D ) TOPOLOGY: linear ( i i ) MOLECULE TYPE: peptide ( v i ) ORIGINAL SOURCE:
      ( A ) ORGANISM: Human immunodeficiency virus ( x i ) SEQUENCE DESCRIPTION: SEQ ID NO:7:

Cys Val Gly Gly Pro Gly His Lys Ala Arg Val Leu
1               5                   10

( 2 ) INFORMATION FOR SEQ ID NO:8:

( i ) SEQUENCE CHARACTERISTICS:
      ( A ) LENGTH: 16 amino acids
      ( B ) TYPE: amino acid
      ( D ) TOPOLOGY: linear ( i i ) MOLECULE TYPE: peptide ( v i ) ORIGINAL SOURCE:
      ( A ) ORGANISM: Human immunodeficiency virus ( x i ) SEQUENCE DESCRIPTION: SEQ ID NO:8:

Asp Leu Asn Thr Met Leu Asn Thr Val Gly Gly His Gln Ala Ala Cys
1               5                   10                  15

( 2 ) INFORMATION FOR SEQ ID NO:9:

(i) SEQUENCE CHARACTERISTICS:
  (A) LENGTH: 16 amino acids
  (B) TYPE: amino acid
  (D) TOPOLOGY: linear (ii) MOLECULE TYPE: peptide (vi) ORIGINAL SOURCE:
  (A) ORGANISM: Human immunodeficiency virus (xi) SEQUENCE DESCRIPTION: SEQ ID NO:9:

```
Val His Gln Ala Ile Ser Pro Arg Thr Leu Asn Ala Trp Val Lys Cys
 1           5                  10                   15
```

(2) INFORMATION FOR SEQ ID NO:10:

(i) SEQUENCE CHARACTERISTICS:
    (A) LENGTH: 15 amino acids
    (B) TYPE: amino acid
    (D) TOPOLOGY: linear (ii) MOLECULE TYPE: peptide (vi) ORIGINAL SOURCE:
    (A) ORGANISM: Human immunodeficiency virus (xi) SEQUENCE DESCRIPTION: SEQ ID NO:10:

```
Cys Gly Ser Glu Glu Leu Arg Ser Leu Tyr Asn Thr Val Ala Thr
 1           5                  10                   15
```

(2) INFORMATION FOR SEQ ID NO:11:

(i) SEQUENCE CHARACTERISTICS:
    (A) LENGTH: 15 amino acids
    (B) TYPE: amino acid
    (D) TOPOLOGY: linear (ii) MOLECULE TYPE: peptide (vi) ORIGINAL SOURCE:
    (A) ORGANISM: Human immunodeficiency virus (xi) SEQUENCE DESCRIPTION: SEQ ID NO:11:

```
Leu Arg Pro Gly Gly Lys Lys Lys Tyr Lys Leu Lys His Ile Val
 1           5                  10                   15
```

HIV-1 CORE PROTEIN FRAGMENTS

This application is a Divisional of Application Ser. No. 07/854,629, filed Jul. 6, 1992, now U.S. Pat. No. 5,480,967, which was filed as International Application Number PCT/GB91/00013, on Jan. 4, 1991.

1. Field of Invention

This invention concerns peptide fragments of HIV (human immunodeficiency virus) and the use thereof in a potential vaccine against AIDS (acquired immune deficiency syndrome), and for diagnostic and therapeutic purposes.

2. Background to the Invention

European Patent Specification No. 0346022 discloses and claims, inter ali, a peptide having the amino acid sequence of a fragment of HIV which interacts specifically with a particular human leucocyte antigen (HLA) class I molecule, to stimulate cytotoxic T lymphocyte immunity.

One such peptide specifically disclosed in the prior application has the sequence $NH_2$-lysine-arginine-tryptophan-isoleucine-isoleucine-leucine-glycine-leucine-asparagine-lysine-isoleucine-valine-arginine-methionine-tyrosine-cysteine-COOH (SEQ ID NO:1), which is derived from the gag (group associated antigen) p24 protein of HIV (i.e. one of the internal core proteins) between residues 263 and 277, and is known as p24-14. The carboxy-terminal cysteine is not part of the gag sequence and is added to facilitate chemical coupling reactions. This peptide interacts specifically with HLA B27, and individuals with HLA B27 (about 7% of the Caucasian population) should respond to the peptide, resulting in production of cytotoxic T lymphocytes (CTL) specific for gag and LA B27, and capable of lysing cells infected with HIV.

The present application concerns further such peptides which have now been identified.

SUMMARY OF THE INVENTION

According to one aspect of the present invention there is provided a peptide having the amino acid sequence of a fragment of HIV which interacts specifically with a particular human leucocyte antigen (HLA) class I molecule, to stimulate cytotoxic T lymphocyte immunity, the peptide having the sequence $NH_2$-valine-glutamine-asparagine-alanine-asparagine-proline-aspartic acid-cysteine-lysine-threonine-isoleucine-leucine-lysine-alanine-leucine-tyrosine-COOH (SEQ ID NO:2).

This sequence is derived from the gag p24 protein of HIV. This peptide, which is known as p24-20, interacts specifically with HLA B8 and individuals with HLA B8 (about 15% of the Caucasian population) should respond to the peptide, resulting in production of cytotoxic T lymphocytes (CTL) specific for gag and HLA B8, and capable of lysing cells infected with HIV. Peptide p24-20 has also been recognised by a seropositive donor of the HLA type HLA-A3, 29B44, 14 and therefore can be recognised in association with one of these HLA molecules as well as HLA-B8.

According to another aspect of the present invention there is provided a peptide having the amino acid sequence of a fragment of HIV which interacts specifically with a particular human leucocyte antigen (HLA) class I molecule, to stimulate cytotoxic T lymphocyte immunity, the peptide having the sequence $NH_2$-cysteine-glycine-serine-glutamic acid-glutamic acid-leucine-arginine-serine-leucine-tyrosine-asparagine-threonine-valine-alanine-threonine-leucine-COOH (SEQ ID NO:3).

This sequence is derived from the gag p17 protein of HIV. This peptide, which is known as p17-8, interacts specifically with HLA A2 and individuals with HLA A2 (about 40% of the Caucasian population) should respond to the peptide, resulting in production of cyotoxic T lymphocytes CTL) specific for gag and HLA A2, and capable of lysing cells infected with HIV.

According to another aspect of the present invention there is provided a peptide having the amino acid sequence of a fragment of HIV which interacts specifically with a particular human leucocyte antigen (HLA) class I molecule, to stimulate cytotoxic T lymphocyte immunity, the peptide having the sequence $NH_2$-cysteine-leucine-arginine-proline-glycine-glycine-lysine-lysine-lysine-tyrosine-lysine-leucine-lysine-histidine-isoleucine-valine-COOH (SEQ ID NO:4).

This sequence is derived from the gag p17 protein of HIV. The amino terminal cysteine is not part of the gag sequence and is added to facilitate chemical coupling reactions. The invention thus also includes within its scope the peptide without the amino terminal cysteine. This peptide, which is known as p17-3, also interacts specifically with HLA B8 and individuals with LA B8 should respond to the peptide, resulting in production of cytotoxic T lymphocytes (CTL) specific for gag and HLA B8, and capable of lysing cells infected with HIV.

Five other epitopes from the gag p24 protein of HIV have also been identified as being able to sensitize targets in the CTL assay, but their HLA restrictions have not yet been fully worked out. Details are given below.

Peptide p24-7 is as follows:

NH2-phenylalanine-arginine-aspartic acid-tyrosine-valine-aspartic acid-arginine-phenylalanine-tyrosine-lysine-threonine-leucine-arginine-alanine-glutamic acid-cysteine-COOH (SEQ ID NO:5). HLA restriction of this peptide is through one or more of the antigens HLA-A3 or A29 or B44 or B14.

Peptide p24-22 is as follows:

$NH_2$-leucine-glutamic acid-glutamic acid-methionine-methionine-threonine-alanine-cysteine-glutamine-glycine-valine-glycine-glycine-proline-glycine-tyrosine-COOH (SEQ ID NO:6). HLA restriction of this peptide is through one or more of the antigens HLA-A3 or A29 or B44 or B14.

Peptide p24-23 is as follows:

$NH_2$-cysteine-valine-glycine-glycine-proline-glycine-histidine-lysine-alanine-arginine-valine-leucine-COOH (SEQ ID NO:7). HLA restriction of this peptide is through one or more of the antigens LA-A1 or B7 or B8.

Peptide p24-6 is as follows:

$NH_2$-aspartic acid-leucine-asparagine-threonine-methionine-leucine-asparagine-threonine-valine-glycine-glycine-histidine-glutamine-alanine-alanine-cysteine-COOH (SEQ ID NO:8). HLA restriction of this peptide is through one or more of antigens HLA-A3 or A29 or B44 or B14.

Peptide p24-2 is as follows:

$NH_2$-valine-histidine-glutamine-alanine-isoleucine-serine-proline-arginine-threonine-leucine-asparagine-alanine-tryptophan-valine-lysine-cysteine-COOH (SEQ ID NO:9). HLA restriction of this peptide is through one or more of antigens HLA-A23 or A30 or B8.

By way of explanation, it has been shown that virus proteins such as gag are presented to T cells as degraded peptide fragments (about 15 amino acids) bound to larger HLA class I molecules on the surface of infected cells. Different peptide regions (epitopes) are recognised and interact specifically with different HLA class I molecules. CTL will only recognise target cells that share HLA Class I molecules, i.e. the T cells recognise a combination of virus antigen plus self HLA. There are probably about 120 different HLA class I molecules, and each individual human has a limited selection, and so will respond only to certain epitopes. Following the example of p24-20, which can be recognised by more than one type of HLA molecule, it is possible the other peptides of the invention may also be restricted by more than one HLA molecule.

The peptides disclosed above all include a region which contains a CTL epitope. It may be possible that one or more individual amino acids in the identified sequences may be altered in naturally occuring variants of the virus, yet still function in the same way, and the invention is intended to cover such and similar variants.

Epitopes recognised with different HLA can be identified and isolated in known manner or made by protein synthesis using known techniques.

Peptides in accordance with the invention can be used as the basis of a vaccine against AIDS, by stimulating production of CTL responsive to the relevant HLA and so priming the CTL response.

In a further aspect the present invention thus provides a vaccine against AIDS, comprising a peptide of the invention.

The vaccine may comprise more than one peptide, and may additionally comprise one or more other peptides responsive to some of the more common HLA class I molecules to increase effectiveness.

The vaccine may take various different forms. For example, the vaccine may comprise a peptide or mixture of peptides for administration in solution, or absorbtion onto insoluble material or mixing with an adjuvant. The peptide amino acid sequence could alternatively be used to construct synthetic or fusion proteins that contain the relevant peptide epitopes, by known recombinant DNA techniques. These proteins could be used to immunise as soluble protein or absorbed onto insoluble material or mixed with adjuvant. Alternatively the sequence information could be used to construct recombinant micro-organisms using known techniques which would express the relevant sequences in their own proteins. Examples would be recombinant vaccinia viruses, recombinant polio myelitis viruses, recombinant BCG, recombinant salmonella, recombinant adenovirus.

Another use of the sequence information would be to construct analogs of the peptides, or other chemicals which would interact with e.g. bind to the HLA molecules involved or the T cell receptors involved and interfere with or stimulate this form of immune response.

Inhibition of this type of immunity might be important if this immune response plays a harmful role in any of the pathology caused by HIV. If so it may be important to regulate the levels of this type of T cell immunity in HIV seropositive individuals so as to achieve a balance between beneficial and harmful effects. Stimulation by such agents may be an alternative way of inducing an immune response in seronegative individuals.

Peptides in accordance with the invention can also be used for diagnostic purposes. In particular, it has been found that it is possible to use such a peptide in some patients to identify T lymphocyte response in a relatively simple assay. Briefly, fresh peripheral blood mononuclear cells (or lymphocytes obtained from biopsy material) are prepared and added at ratios of 50:1, 25:1 and 10:1 to $10^4$ $^{51}$-chromium labelled B lymphoblastoid cells matched for the relevant HLA molecules. The HLA type of patient is determined in known manner by tissue typing, and B lymphoblastoid cells obtained from a donor of known HLA type (again determined in known manner by tissue typing) and transformed with Epstein Barr using known techniques. A peptide in accordance with the invention, which interacts with the relevant HLA molecule, is also added to the cells in a concentration of 10 to 100 u molar. After 4 hours incubation the supernatant is removed and the released $^{51}$-chromium measured. The $^{51}$-chromium released is compared to that released by incubation of labelled cells in detergent, which gives a maximum value, and released by labelled cells incubated in medium alone, which gives a minimum value. If lysis (defined by $^{51}$-chromium released of at least two times the minimum value) is observed it means that there are cytotoxic T lymphocytes in the patients' mononuclear cells and these are likely to be indicative of infection with HIV.

Such an assay, together with antibody measurements, may also be useful for measurement of the patient's general immune response to HIV, and may have prognostic implications. This approach may represent a very simple method which can be used for measuring cell mediated immunity in HIV seropositive patients. It may also be possible to automate the method.

Hence, in a further aspect the present invention provides a method of assaying cells for the presence of cytotoxic T lymphocytes, comprising incubating cells with labelled B lymphoblastoid cells matched for HLA type in the presence of a peptide of the invention which interacts with the relevant HLA type, and determining the amount of label released.

By comparing the amount of released label with known standards an indication of the degree of lysis can be obtained and hence of likely infection with IV.

Peptides of the invention may also have potential use in therapy. These and similar peptides (and other peptide epitodes that have been identified previously in studies on influenza virus) have been used to stimulate cytotixic T lymphocytes to grow in vitro. The method involves exposing cultured peripheral blood mononuclear cells or B lymphoblastoid cell lines, which have been treated for one hour with an appropriate peptide at approximately 10–100 ug/ml then washed in tissue culture medium and irradiated to 3000 rads. The cells are then cultured in the presence of interleukin-2 at 10 units/ml. Using this method cytotoxic T lymphocyte cell lines specific for the peptide have been grown, and these lines have been expanded up to $10^8$ cells. These expanded cytotoxic T cell lines could be used to treat patients by reinfusion.

Preliminary data indicates that patients with AIDS or the AIDS related complex show low levels of cytotoxic T cell activity, whereas those who are infected with HIV but are healthy show high levels. Part of the immune deficiency syndrome therefore may be a result of impaired cytotoxic T cell activity. The proposal therefore would be to reinfuse autologous cytotoxic T cells grown in vitro on synthetic peptide pulsed cells. Initially patients who had previously had a high cytotoxic T cell activity would be treated at a stage when their levels of these cells was declining. The cytotoxic T cell lines could be prepared from frozen lymphocytes taken earlier in the patient's infection.

Thus in another aspect the invention provides a method of treating a patient for AIDS or related conditions, comprising administering cytotoxic T cells treated with a peptide in accordance with the invention which interacts with a HLA molecule present in the patient.

The cytotoxic T cells are preferably derived from lymphocytes taken from the patient at an earlier stage. The lymphocytes may be stored in frozen condition until used for preparation of the cytotoxic T cell line.

In addition it may be useful to treat patients for AIDS or related conditions by vaccination with a peptide in accordance with the invention.

The peptide epitope p24-12 is found to be quite well conserved between different strains of HIV 1 and HIV 2, and it was found that cytotoxic T lymphocytes from a patient infected with HIV 1 cross-reacted on the HIV 2 peptide sequence. Similar properties may apply to the peptides of the invention. In this case, the peptide of the invention may be useful in vaccines to stimulate protection against both HIV 1 and HIV 2, and also for diagnostic and therapeutic purposes with patients infected with HIV 1 and/or HIV 2.

What is claimed as new and desired to be secured by letters patent of the United States is:

1. A pharmaceutical composition, comprising:
  (A) a pharmaceutically acceptable carrier; and
  (B) a peptide selected from the group consisting of:
    (1) a peptide having the amino acid sequence NH$_2$-valine-glutamine-asparagine-alanine-asparagine-proline-aspartic acid-cysteine-lysine-threonine-isoleucine-leucine-lysine-alanine-leucine-tyrosine COOH (SEQ ID NO:2);
    (2) a peptide having the amino acid sequence NH$_2$-cysteine-glycine-serine-glutamic acid-glutamic acid-leucine-arginine-serine-leucine-tyrosine-asparagine-threonine-valine-alanine-threonine-COOH (SEQ ID NO:10);
    (3) a peptide having the amino acid sequence NH$_2$-leucine-arginine-proline-glycine-glycine-lysine-lysine-lysine-tyrosine-lysine-leucine-lysine-histidine-isoleucine-valine -COOH (SEQ ID NO:11);
    (4) a peptide having the amino acid sequence NH$_2$-cysteine-leucine-arginine-proline-glycine-glycine-lysine-lysine-lysine-tyrosine-lysine-leucine-lysine-histidine -isoleucine-valine-COOH (SEQ ID NO:4);
    (5) a peptide having the amino acid sequence NH$_2$-phenylalanine-arginine-aspartic acid-tyrosine-valine-aspartic acid-arginine-phenylalanine-tyrosine-lysine-threonine -leucine-arginine-alanine-glutamic acid-cysteine-COOH (SEQ ID NO:5);
    (6) a peptide having the amino acid sequence NH$_2$-leucine-glutamic acid-glutamic acid-methionine-methionine-threonine-alanine-cysteine-glutamine-glycine-valine-glycine-glycine-proline-glycine-tyrosine-COOH (SEQ ID NO:6);
    (7) a peptide having the amino acid sequence NH$_2$-cysteine-valine-glycine -glycine-proline-glycine-histidine-lysine-alanine-arginine-valine-leucine-COOH (SEQ ID NO:7);
    (8) a peptide having the amino acid sequence NH$_2$-aspartic acid-leucine -asparagine-threonine-methionine-leucine-asparagine-threonine-valine-glycine-glycine -histidine-glutamine-alanine-alanine-cysteine-COOH (SEQ ID NO:8); and
    (9) a peptide having the amino acid sequence NH$_2$-valine-histidine-glutamine -alanine-isoleucineserine-proline-arginine-threonine-leucine-asparagine-alanine-tryptophan-valine-lysine-cysteine-COOH (SEQ ID NO:9).

2. The pharmaceutical composition of claim 1, wherein said peptide has the amino acid sequence NH$_2$-valine-glutamine-asparagine-alanine-asparagine-proline-aspartic acid-cysteine-lysine-threonine-isoleucine-leucine-lysine-alanine-leucine-tyrosine COOH (SEQ ID NO:2).

3. The pharmaceutical composition of claim 1, wherein said peptide has the amino acid sequence NH$_2$-cysteine-glycine-serine-glutamic acid-glutamic acid-leucine-arginine-serine-leucine-tyrosine-asparagine-threonine-valine-alanine-threonine-COOH (SEQ ID NO:10).

4. The pharmaceutical composition of claim 1, wherein said peptide has the amino acid sequence sequence NH$_2$-leucine-arginine-proline-glycine-glycine-lysine-lysine-lysine -tyrosine-lysine-leucine-lysine-histidine-isoleucine-valine-COOH (SEQ ID NO:11 ).

5. The pharmaceutical composition of claim 1, wherein said peptide has the amino acid sequence NH$_2$-cysteine-leucine-arginine-proline-glycine-glycine-lysine-lysine-lysine -tyrosine-lysine-leucine-lysine-histidine-isoleucine-valine-COOH (SEQ ID NO:4).

6. The pharmaceutical composition of claim 1, wherein said peptide has the amino acid sequence NH$_2$-phenylalanine-arginine-aspartic acid-tyrosine-valine-aspartic acid-arginine-phenylalanine-tyrosine-lysine-threonine-leucine-arginine-alanine-glutamic acid-cysteine-COOH (SEQ ID NO:5).

7. The pharmaceutical composition of claim 1, wherein said peptide has the amino acid sequence NH$_2$-leucine-glutamic acid-glutamic acid-methionine-methionine-threonine -alanine-cysteine-glutamine-glycine-valine-glycine-glycine-proline-glycine-tyrosine-COOH (SEQ ID NO:6).

8. The pharmaceutical composition of claim 1, wherein said peptide has the amino acid sequence NH$_2$-cysteine-valine-glycine-glycine-proline-glycine-histidine-lysine-alanine -arginine-valine-leucine-COOH (SEQ ID NO:7).

9. The pharmaceutical composition of claim 1, wherein said peptide has the amino acid sequence NH$_2$-aspartic acid-leucine-asparagine-threonine-methionine-leucine -asparagine-threonine-valine-glycine-glycine-histidine-glutamine-alanine-alanine-cysteine -COOH (SEQ ID NO:8).

10. The pharmaceutical composition of claim 1, wherein said peptide has the amino acid sequence NH$_2$-valine-histidine-glutamine-alanine-isoleucine-serine-proline-arginine -threonine-leucine-asparagine-alanine-tryptophan-valine-lysine-cysteine-COOH (SEQ ID NO:9).

11. A method of assaying a sample of cells for the presence of cytotoxic T lymphocytes, said method comprising:

(i) incubating said sample of cells with labeled B lymphoblastoid target cells matched for HLA type in the presence of a peptide for a time and under conditions sufficient to result in release of label;

(ii) determining the amount of label released; and (iii) correlating the amount of label released with the number of cytotoxic T lymphocytes present in said sample of cells, wherein said peptide is selected from the group consisting of:

(1) a peptide having the amino acid sequence NH$_2$-valine-glutamine -asparagine-alanine-asparagine-proline-aspartic acid-cysteine-lysine-threonine-isoleucine -leucine-lysine-alanine-leucine-tyrosine COOH (SEQ ID NO:2);

(2) a peptide having the amino acid sequence NH$_2$-cysteine-glycine-serine -glutamic acid-glutamic acid-leucine-arginine-serine-leucine-tyrosine-asparagine-threonine -valine-alanine-threonine-COOH (SEQ ID NO:10);

(3) a peptide having the amino acid sequence NH$_2$-leucine-arginine-proline -glycine-glycine-lysine-lysine-lysine-tyrosine-lysine-leucine-lysine-histidine-isoleucine-valine -COOH (SEQ ID NO:11);

(4) a peptide having the amino acid sequence NH$_2$-cysteine-leucine-arginine -proline-glycine-glycine-lysine-lysine-lysine-tyrosine-lysine-leucine-lysine-histidine-isoleucine-valine-COOH (SEQ ID NO:4);

(5) a peptide having the amino acid sequence NH$_2$-phenylalanine-arginine -aspartic acid-tyrosine-valine-aspartic acid-arginine-phenylalanine-tyrosine-lysine-threonine -leucine-arginine-alanine-glutamic acid-cysteine-COOH (SEQ ID NO:5);

(6) a peptide having the amino acid sequence NH$_2$-leucine-glutamic acid -glutamic acid-methionine-methionine-threonine-alanine-cysteine-glutamine-glycine-valine -glycine-glycine-proline-glycine-tyrosine-COOH (SEQ ID NO:6);

(7) a peptide having the amino acid sequence NH$_2$-cysteine-valine-glycine -glycine-proline-glycine-histidine-lysine-alanine-arginine-valine-leucine-COOH (SEQ ID NO:7);

(8) a peptide having the amino acid sequence NH$_2$-aspartic acid-leucine -asparagine-threonine-methionine-leucine-asparagine-threonine-valine-glycine-glycine -histidine-glutamine-alanine-alanine-cysteine-COOH (SEQ ID NO:8); and (9) a peptide having the amino acid sequence NH$_2$-valine-histidine-glutamine -alanine-isoleucine-serine-proline-arginine-threonine-leucine-asparagine-alanine-tryptophan -valine-lysine-cysteine-COOH (SEQ ID NO:9).

12. The method of claim 11, wherein said peptide has the amino acid sequence NH$_2$-valine-glutamine-asparagine-alanine-asparagine-proline-aspartic acid-cysteine-lysine -threonine-isoleucine-leucine-lysine-alanine-leucine-tyrosine COOH (SEQ ID NO:2).

13. The method of claim 11, wherein said peptide has the amino acid sequence NH$_2$-cysteine-glycine-serine-glutamic acid-glutamic acid-leucine-arginine-serine-leucine-tyrosine -asparagine-threonine-valine-alanine-threonine-COOH (SEQ ID NO:10).

14. The method of claim 11, wherein said peptide has the amino acid sequence NH$_2$-leucine-arginine-proline-glycine-glycine-lysine-lysine-lysine-tyrosine-lysine-leucine-lysine -histidine-isoleucine-valine-COOH (SEQ ID NO:11 ).

15. The method of claim 11, wherein said peptide has the amino acid sequence NH$_2$-cysteine-leucine-arginine-proline-glycine-glycine-lysine-lysine-lysine-tyrosine-lysine-leucine -lysine-histidine-isoleucine-valine-COOH (SEQ ID NO:4).

16. The method of claim 11, wherein said peptide has the amino acid sequence NH$_2$-phenylalanine-arginine-aspartic acid-tyrosine-valine-aspartic acid-arginine-phenylalanine -tyrosine-lysine-threonine-leucine-arginine-alanine-glutamic acid-cysteine-COOH (SEQ ID NO:5).

17. The method of claim 11, wherein said peptide has the amino acid sequence NH$_2$-leucine-glutamic acid-glutamic acid-methionine-methionine-threonine-alanine-cysteine -glutamine-glycine-valine-glycine-glycine-proline-glycine-tyrosine-COOH (SEQ ID NO:6).

18. The method of claim 11, wherein said peptide has the amino acid sequence NH$_2$-cysteine-valine-glycine-glycine-proline-glycine-histidine-lysine-alanine-arginine-valine-leucine-COOH (SEQ ID NO:7).

19. The method of claim 11, wherein said peptide has the amino acid sequence NH$_2$-aspartic acid-leucine-asparagine-threonine-methionine-leucine-asparagine-threonine-valine-glycine-glycine-histidine-glutamine-alanine-alanine-cysteine-COOH (SEQ ID NO:8).

20. The method of claim 11, wherein said peptide has the amino acid NH$_2$-valine-histidine-glutamine-alanine-isoleucine-serine-proline-arginine-threonine-leucine-asparagine-alanine-tryptophan-valine-lysine-cysteine-COOH (SEQ ID NO:9).

21. The method of claim 11, wherein said labeled B lymphoblastoid target cells have been incubated with $^{51}$Cr.

* * * * *